United States Patent [19]

Sims

[11] Patent Number: 5,285,224
[45] Date of Patent: Feb. 8, 1994

[54] METHODS AND APPARATUS FOR DETERMINING REFRACTIVE ERROR

[76] Inventor: Clinton N. Sims, 3432 West Riverside Dr., Ft. Myers, Fla. 33901

[21] Appl. No.: 893,245

[22] Filed: Jun. 3, 1992

Related U.S. Application Data

[63] Continuation-in-part of Ser. No. 526,395, May 21, 1990, Pat. No. 5,120,124, which is a continuation-in-part of Ser. No. 427,724, Oct. 27, 1989, Pat. No. 5,104,214, which is a continuation-in-part of Ser. No. 310,334, Feb. 13, 1989, Pat. No. 4,943,162, which is a continuation-in-part of Ser. No. 116,322, Nov. 2, 1987, Pat. No. 4,840,479, which is a continuation-in-part of Ser. No. 23,980, Mar. 16, 1987, Pat. No. 4,820,040, which is a continuation of Ser. No. 670,398, Nov. 9, 1984, abandoned.

[51] Int. Cl.$^5$ .......................... A61B 3/02; G02B 27/02
[52] U.S. Cl. .................................. 351/235; 351/233; 359/441; 359/809
[58] Field of Search ............... 351/233, 235, 216, 234; 359/812, 813, 827, 888, 889, 891, 809, 440, 441, 442

[56] References Cited

U.S. PATENT DOCUMENTS

| | | |
|---|---|---|
| 579,132 | 8/1897 | Clark . |
| 1,222,017 | 4/1917 | Moseley . |
| 1,266,224 | 5/1918 | Day . |
| 1,337,265 | 4/1920 | Poser . |
| 1,550,582 | 8/1925 | Sheard . |
| 1,594,196 | 7/1926 | Herold et al. . |
| 1,794,571 | 3/1931 | Wrighton et al. . |
| 2,147,448 | 2/1939 | Lee . |
| 2,256,491 | 9/1941 | Peck et al. . |
| 2,333,738 | 11/1943 | Peck et al. . |
| 2,746,346 | 5/1956 | Gaire ............................ 359/442 |
| 2,874,610 | 2/1959 | Wright . |
| 2,923,200 | 2/1960 | Wright . |
| 2,938,426 | 5/1960 | Armbruster et al. . |
| 2,968,213 | 1/1961 | Wright et al. . |
| 2,995,065 | 8/1961 | Wright et al. . |
| 3,015,984 | 1/1962 | Hemstreet . |
| 3,136,839 | 6/1964 | Safir ............................ 88/56 |
| 3,163,940 | 1/1965 | Geiser ............................ 359/442 |
| 3,415,594 | 12/1968 | Aulhorn ............................ 351/30 |
| 3,428,398 | 2/1969 | Gottschalk ............................ 355/52 |
| 3,498,699 | 3/1970 | Wilkenson ............................ 351/235 |
| 3,524,702 | 8/1970 | Bellows et al. ............................ 351/6 |
| 3,572,908 | 3/1971 | Grolman ............................ 351/6 |
| 3,602,580 | 8/1971 | Samuels ............................ 351/6 |
| 3,664,631 | 5/1972 | Guyton ............................ 351/27 |
| 3,785,723 | 1/1974 | Guyton ............................ 351/34 |

(List continue on next page.)

FOREIGN PATENT DOCUMENTS 598683 5/1960 Canada .
820766 9/1959 United Kingdom .

OTHER PUBLICATIONS

Stokes, "On a Mode of Measuring the Astigmatism of a Defective Eye" (1983).

Dennett, "The Stokes' Lens for Measuring Astigmatism" (1985).

Jackson, "A Trial Set of Small Lenses in a Modified Trial Frame" (1887).

(List continue on next page.)

Primary Examiner—Loha Ben
Attorney, Agent, or Firm—Kilpatrick & Cody

[57] ABSTRACT

Methods and apparatus for measuring or determining refractive errors are disclosed. In some embodiments the invention includes two bars, each containing multiple lenses positioned longitudinally along the bar, and a collar adapted to constrain relative movement of the bars. Moving, or sliding, the bars and collar positions various lenses in the patient's line of sight, permitting the patient to determine which combination produces the best vision. If asymmetrical lenses are included in either bar, rotating the appropriate lens (either directly or by rotating the bar) provides additional information concerning the optimal refractive correction. The collar or bar may further comprise an indicator for signifying the angular rotation of any asymmetrical lens positioned along the patient's line of sight.

12 Claims, 3 Drawing Sheets

U.S. PATENT DOCUMENTS

| | | | |
|---|---|---|---|
| 3,791,719 | 2/1974 | Kratzer et al. | 351/11 |
| 3,819,256 | 6/1974 | Bellows et al. | 351/6 |
| 3,822,932 | 7/1974 | Humphrey | 351/17 |
| 3,832,066 | 8/1974 | Cornsweet | 356/127 |
| 3,841,760 | 10/1974 | Guyton | 356/124 |
| 3,860,330 | 1/1975 | Persson | 351/29 |
| 3,874,774 | 4/1975 | Humphrey | 351/26 |
| 3,880,502 | 4/1975 | Humphrey | 351/39 |
| 3,883,233 | 5/1975 | Guilino | 351/6 |
| 3,969,020 | 7/1976 | Lynn et al. | 351/17 |
| 4,015,899 | 4/1977 | Humphrey | 351/233 |
| 4,021,102 | 5/1977 | Iizuka | 351/13 |
| 4,105,302 | 8/1978 | Tate, Jr. | 351/7 |
| 4,179,196 | 12/1979 | Persson et al. | 351/30 |
| 4,180,323 | 12/1979 | Persson et al. | 356/3 |
| 4,185,896 | 1/1980 | Buhler | 351/29 |
| 4,190,332 | 2/1980 | Body et al. | 351/13 |
| 4,215,919 | 8/1990 | Rybicki | 351/29 |
| 4,385,813 | 5/1983 | Klein et al. | 351/235 |
| 4,413,891 | 11/1983 | Rybicki | 351/235 |
| 4,426,140 | 1/1984 | Stephens | 351/204 |
| 4,436,390 | 3/1984 | Aoki | 351/234 |
| 4,496,226 | 1/1985 | Augusto et al. | 351/234 |
| 4,523,822 | 6/1985 | Thurston | 351/235 |
| 4,606,524 | 8/1986 | Wood | 351/234 |
| 4,746,955 | 5/1988 | Slayton et al. | 359/889 |
| 5,122,911 | 6/1992 | Kuo | 359/889 |
| 5,791,132 | 8/1897 | Clark . | |

OTHER PUBLICATIONS

"Dr. Thomson's 1895 Correspondence Course in Optics with Historical Commentary by Monroe J. Hirsch".

Friedman, "The Jackson Crossed Cylinder, A Critique" (1940).

Crisp, "A New Cross-Cylinder Test for Astigmatic Axis, Without Use of Test Type" (1942).

Egan, "A Resume of Crossed Cylinder Application and Theory".

Littmann, "Fundamental Considerations About Opthalmometry".

Wunsh, "The Crossed Cylinder" (chapter 38 of Clinical Ophthalmology (vol 1), Duane, editor (1978).

Kaufman, "Subjective Refraction: Fogging Use of the Astigmatic Dials" (chapter 39 of Clinical Ophthalmology (vol. 1), Duane, editor (1978).

Duke-Elder and Abrams, "Ophthalmic Optics in Refraction" (1970) pp. 438–439.

Alverez, "Development of Variable-Focus Lenses and a New Refractor" (1978).

Michaels, Visual Optics and Refraction (chapter 12) (1980).

Guyton, "Automated Clinical Refraction" (chapter 67 of Clinical Opthalmology (vol. 1)), Duane, editor (1985).

Chapter 67 of "Clinical Ophthalmology," vol. 1, edited by Duane and Jaeger (1986).

Section 36 of Donders, "Accommodation and Refraction of the Eye" (1860 or 1864).

Page 12263 of "The American Encyclopedia and Dictionary of Ophthalmology," vol. 16, edited by Wood (1920).

pp. 7195–7197 of "The American Encyclopedia and Dictionary of Ophthalmology," vol. 10, edited by Wood (1917).

p. 438 in vol. 5 of "System of Ophthalmology," entitled *Ophthalmic Optics and Refraction*, by Duek-Elder and Agrams (1970).

An advertisement of Stereo Optical Co., Inc. entitled "New Sensitivity for Routine Amsler Grid Testing".

A brochure of Stereo Optical Co., Inc. entitled "Polarized Threshold Amsler Grid System".

pp. 449–465 of "System of Diseases of the Eye," vol. 4, edited by Norris and Oliver (1900).

Chapters V and VIII-XII of Thorington, *Refraction and How to Refract*, P. Blakiston's Son & Co. (1900).

METHODS AND APPARATUS FOR DETERMINING REFRACTIVE ERROR

CROSS-REFERENCE TO RELATED APPLICATIONS

This application is a continuation-in-part of U.S. application Ser. No. 07/526,395 (to issue as U.S. Pat. No. 5,120,124), filed May 21, 1990, entitled "Devices for Determining the Crossed Cylinder Powers and Axes for Multiple Lens Sets," which application is a continuation-in-part of U.S. application Ser. No. 07/427,724 (now U.S. Pat. No. 5,104,214), filed Oct. 27, 1989, entitled "Trial Frames, Adjustable Spectacles and Associated Lens Systems," which application is a continuation-in-part of U.S. application Ser. No. 07/310,334 (now U.S. Pat. No. 4,943,162), filed Feb. 13, 1989, entitled "Astigmatic Self-Refractor and Method of Use," which application is a continuation-in-part of U.S. application Ser. No. 07/116,322 (now U.S. Pat. No. 4,840,479) filed Nov. 2 1987 entitled "Crossed Cylinder Lenses Refractor with Three-lens Variable Crossed Cylinder Assembly and Method of Use," which application is a continuation-in-part of U.S. application Ser. No. 07/023,980 (now U.S. Pat. No. 4,820,040), filed Mar. 16, 1987, entitled "Crossed Cylinder Lenses Refractor and Method of Use," which application is a continuation of U.S. application Ser. No. 06/670,398, filed Nov. 9, 1984, now abandoned, all of which applications are incorporated herein in their entireties by this reference.

FIELD OF THE INVENTION

The present invention relates to subjective apparatus and methods for measuring or determining optical errors in the eyes of humans and more particularly to one or more bars and associated equipment containing multiple cylinder, crossed cylinder, or other lenses.

SUMMARY OF THE INVENTION

The present invention provides a simpler and inexpensive alternative to refractors, trial frames, and other equipment and devices typically used by practitioners to determine the optical (including astigmatic) errors of their patients. In one embodiment, the invention includes two bars, each containing multiple lenses positioned longitudinally along the bar, and a collar adapted to constrain relative movement of the bars when desired. Moving, or sliding, the bars and collar positions various lenses in the patient's line of sight, permitting the patient to determine which combination produces the best vision. If asymmetrical lenses ar included in either bar, rotating the appropriate lens (either directly or by rotating the bar) provides additional information concerning the optimal refractive correction. The collar may also include an opening for receiving a removable lens if placement of as many as three lenses before a patient is required. Either the collar or bar may further comprise means for determining the angular rotation of the asymmetrical lens positioned along the patient's line of sight.

It is therefore an object of the present invention to provide at least one bar or frame, containing multiple lenses positioned longitudinally along the bar or frame, as an optical diagnostic tool.

It is a further object of the present invention to provide means such as a collar for constraining the relative movement of two (or more) bars, each containing multiple lenses.

It is another object of the present invention to provide for rotation of asymmetrical lenses contained in one or more bars.

It is another object of the present invention to provide a removable lens adapted to be aligned with lenses of one or more bars along a patient's line of sight.

Other objects, features, and advantages of the present invention will become apparent with reference to the remainder of the written portion and the drawings of this application.

DETAILED DESCRIPTION

1. Structure

Figure 1:
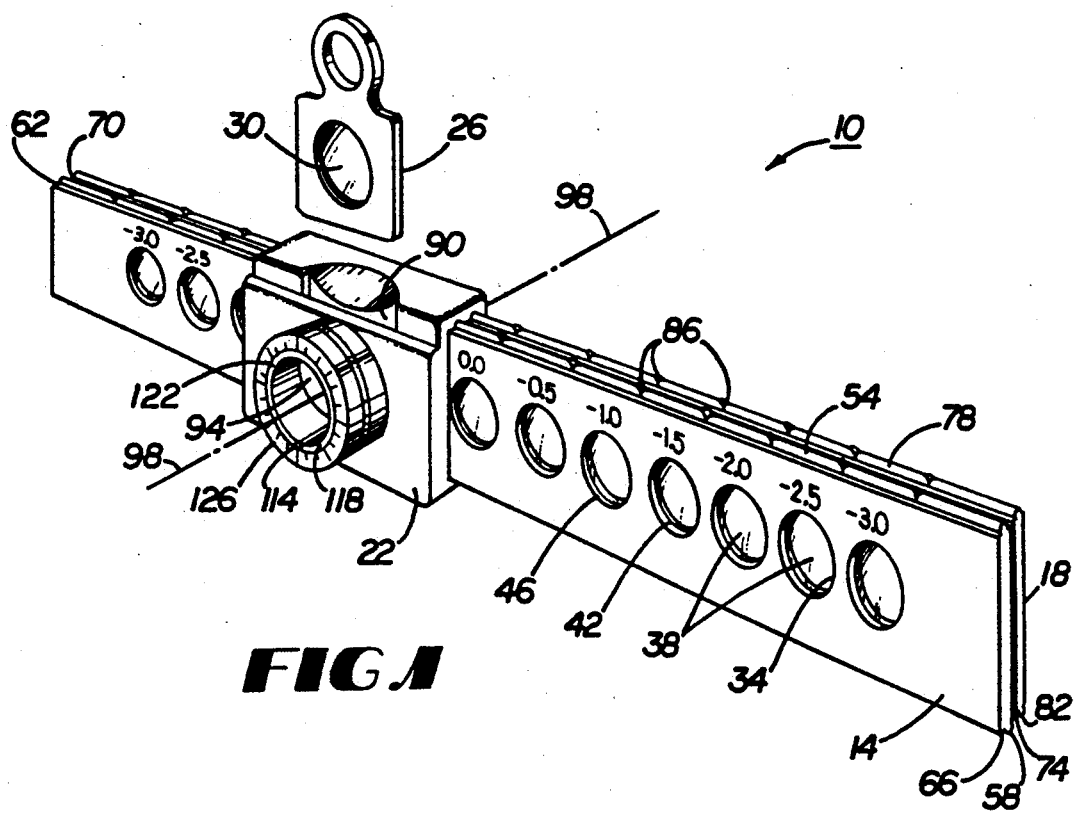
FIG. 1 is a perspective view of an embodiment of the present invention illustrating, e.g., two lens bars, a removable lens, and a collar which is moveable relative to the lens bars.

FIG. 1 illustrates an embodiment of the optical apparatus 10 of the present invention. Apparatus 10 includes first and second lens bars 14 and 18, respectively, and collar 22. Also shown in FIG. 1 is frame 26 for housing lens 30. As described herein, apparatus 10 may be used to determine the optical error of a patient, and it and the other embodiments of the invention shown in FIGS. 1-5 are compatible with refractors, trial frames, and numerous other existing and proposed diagnostic and corrective devices. Alternatively, apparatus 10 may be used by itself as a diagnostic tool for determining, e.g., a patient's spherical and astigmatic optical error.

Figure 2:
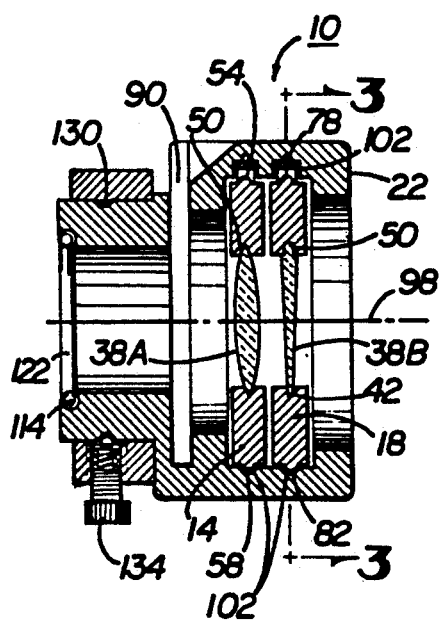
FIG. 2 is a cross-sectional view of the two lens bars and the collar shown attached to an eyepiece such as either of those illustrated in FIG. 4.

Each of lens bars 14 and 18 of FIG. 1-2 defines multiple apertures 34, spaced longitudinally, into which lenses 38 of various types can be placed. FIG. 2, for example, illustrates a sphere lens 38A positioned in an aperture 34 of lens bar 14 and a cylinder lens 38B placed in a corresponding aperture 34 of lens bar 18. In an embodiment of apparatus 10 consistent with FIGS. 1-3, lenses 38 of lens bar 14 are sphere lenses of differing power ($\pm 3.0$ D). Lenses 38 of lens bar 18, by contrast, are cylinder or crossed cylinder lenses of differing powers (0-3.0 D), some having $+90°$ and $-180°$ meridians of greatest lens power and other having greatest power in the $-90°$ and $+180°$ meridians. Apertures 34 may house other types and powers of lens 38, however, including any of those disclosed in my patents and applications incorporated by reference above.

If permanent placement of lenses 38 in lens bars 14 and 18 is desired, the peripheries 42 of the lenses 38 may be adhered to the corresponding peripheries 46 of apertures 34. Alternatively, lenses 38 may merely be snapped into recesses 50 (FIG. 2) of lens bars 14 and 18

(or friction-fitted into apertures 34 if, for example, recesses 50 are absent). Temporary placement of lenses 38 permits their removal or replacement as desired.

Figure 3:
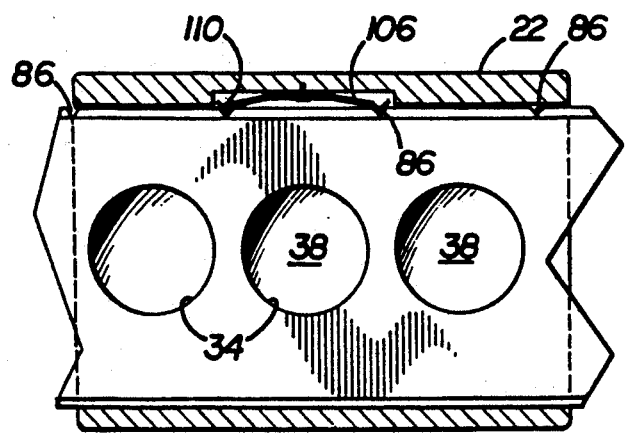
FIG. 3 is a cross-sectional view taken along lines 3—3 of FIG. 2.

Also as shown in FIGS. 1-3, tracks 54 and 58 are formed longitudinally along each of the upper (62) and lower (66) surfaces of lens bar 14. The respective upper and lower surfaces 70 and 74 of lens bar 18 similarly define tracks 78 and 82, with tracks 54 and 78 each including notches 86 spaced at regular intervals. When lens bars 14 and 18 are placed adjacent one another with their upper (62 and 70) and lower (66 and 74) surfaces aligned (as in FIG. 1), the longitudinally-spaced apertures 34 and notches 86 of the lens bars 14 and 15 likewise align.

Collar 22 is designed to constrain movement of lens bars 14 and 18 relative to each other. Collar 22 also is adapted to receive, in pocket 90, frame 26 when lens 30 is needed or desired. Use of lens 30 permits as many as three lenses of similar or differing types, powers, or axes to be aligned in collar aperture 94 for placement along a patient's line of sight 98. To constrain relative movement of lens bars 14 and 18, collar 22 includes recesses 102 for engagement by tracks 54, 58, 78, and 82 and a leaf spring 106 for concurrently engaging notches 86 of both lens bars 14 and 18. Notches 86 and leaf spring 106 form detent 110 for fixing the positions of each of collar 22, first lens bar 14, and second lens bar 18 relative to the others. Disengaging leaf spring 106 from a particular set of notches 86, however, not only permits lens bars 14 and 18 to be repositioned longitudinally relative to each other, but also allows collar 22 to move, or slide, longitudinally relative to both of the lens bars 14 and 18. Thus, component movement of apparatus 10 resembles, in some respects, a conventional slide rule.

If either first lens bar 14 or second lens bar 18 (or both) includes non-spherical lenses 38 (as in FIG. 2), rotation of apparatus 10 about an axis coincident with line of sight 98 may be necessary to achieve optimal diagnostic results. Collar 22, therefore, includes a mercury bead 114 and viscous fluid 118 contained within a annular tube 122. Together with scale 126, the position of bead 114 within tube 122 can be used to determine the angular rotation of lenses 38 of apparatus 10 about line of sight 98. Those ordinarily skilled in the art will recognize, however, that a compass or a variety of other rotation measuring devices may be used in place of bead 114, fluid 118, and tube 122. Collar 22 also include annular recess 130 for attachment to the latching mechanism 134 of a patient-positioning device 138 (FIG. 4) or other suitable equipment.

Figure 4:
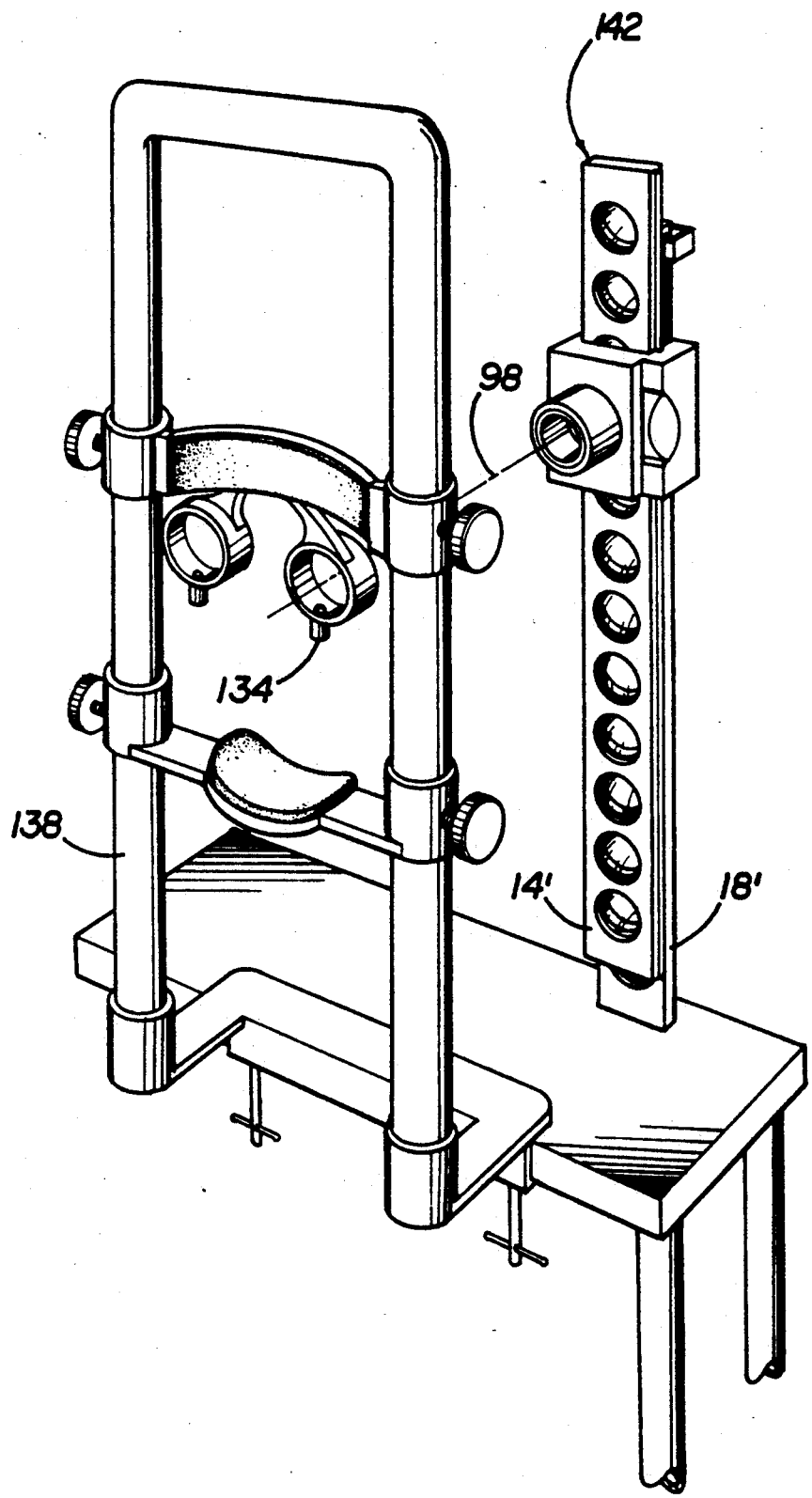
FIG. 4 is a perspective view of an alternate embodiment of the present invention shown with a patient-positioning device including a pair of eyepieces.

FIG. 4 details an alternate apparatus 142 including first and second lens bars 14' and 18'. According to FIG. 4, lens bar 14' is identical to lens bar 14. Either or both of lens bars 14' and 18' may include the rack 144 shown in FIGS. 5-6, however, when, for example, two sets of lenses having cylindrical components are desired. FIG. 4 also illustrates a patient-positioning device 138 and alignability of collar 22 (and selected lenses 38 of lens bars 14' and 18') along line of sight 98. As noted above, latching mechanism 134 may be used to attach collar 22 to device 138.

Figure 5:
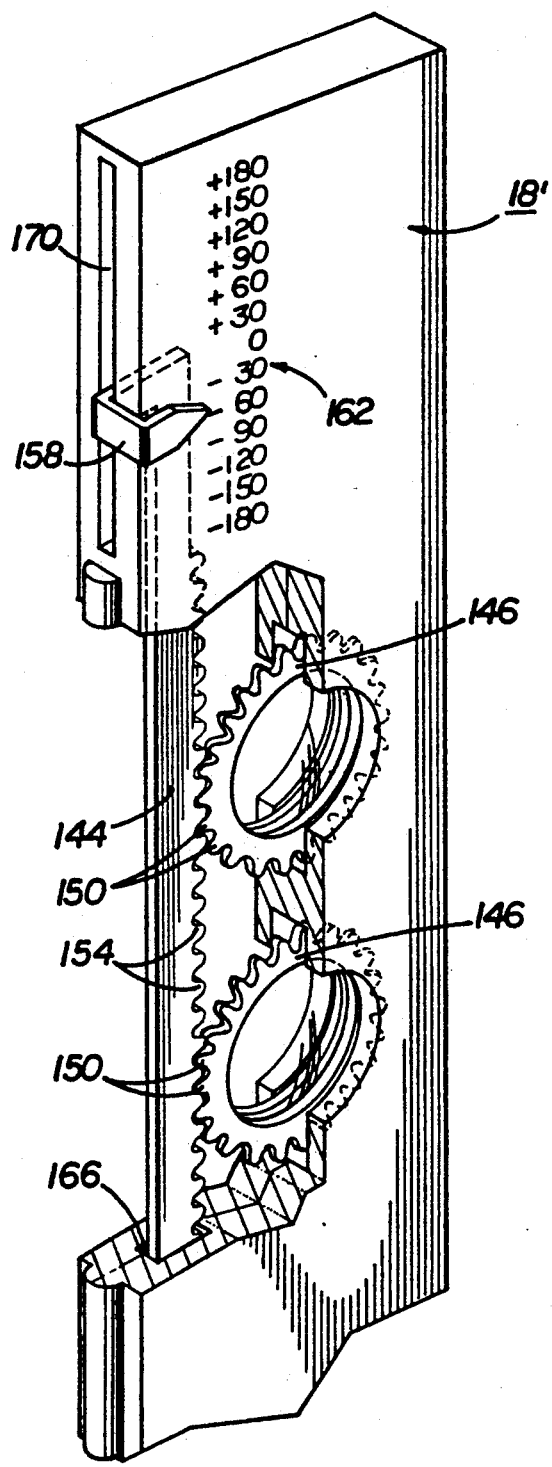
FIG. 5 is a perspective, partially cut-away view of an alternate lens bar for use in connection with the present invention.
Figure 6:
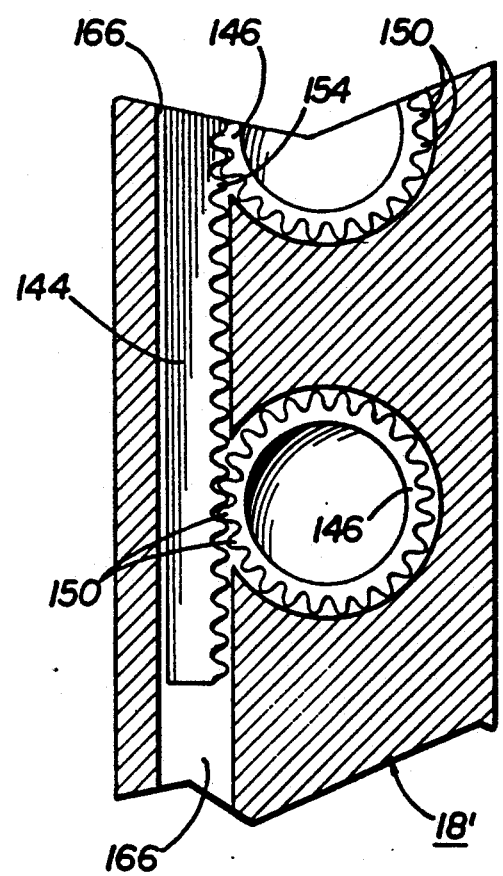
FIG. 6 is a cross-sectional view of a portion of the lens bar of FIG. 5.

Annuli 146, each including a series of teeth 150, encircle lenses 38 in lens bar 18' of FIGS. 5-6. Teeth 150 mesh with complementary teeth 154 of rack 144 so that, when lever 158 of rack 144 is moved, lenses 38 rotate. Lever 158, in conjunction with scale 162 of lens bar 18', also may function as an indicator of the angular rotation of lenses 38. As shown in FIGS. 5-6, rack 144 moves inside a longitudinal slot 166 within lens bar 18', while lever 158 is free to move within a cooperating external slot 170.

2. Operation

Referring to FIG. 1, one embodiment of apparatus 10 has in lens bar 14 sphere lenses 38A with powers ranging in 0.5 D increments from ±3.0 D. Two groups of cylinder lenses 38B, each with powers ranging from 0.5-3.0 D, the first group having axes of greatest power in the +90° and −180° meridians and the second having axes of greatest power in the −90° and +180° meridians, are present in lens bar 18. A (blank) lens 38 of power 0.0 D is also present in lens bar 18. To determine the appropriate optical correction for a patient having astigmatic error using this embodiment of apparatus 10, the practitioner or patient initially moves collar 22 so that the lens 38 of lens bar 18 having power 0.0 D (i.e. the blank lens) is aligned with collar aperture 94. Using force sufficient to dislodge leaf spring 106 from notches 86 of lens bar 14, and while collar aperture 94 is aligned with the patient's line of sight 98, the practitioner, or, preferably, the patient then slides lens bar 14 until the sphere lens 38A providing the optimal vision is aligned with collar aperture 94. The practitioner or patient may note the power of the selected sphere lens 38A and follow by similarly sliding lens bar 18 until the lens 38 providing the best vision also is aligned with collar aperture 94 (and noting its power and meridians as well). At that point, apparatus 10 may be rotated about line of sight 98, thereby rotating the particular cylinder lens 38B of lens bar 18 visible within collar aperture 94, until optimal vision is achieved. The practitioner may then view the position of bead 114 relative to scale 126 to determine the amount of rotation of apparatus 10 which has occurred. From this information an appropriate optical correction may be derived.

Operation of apparatus 142 is in most respects similar. Rather than physically rotating the apparatus, however, the patient or practitioner need merely manipulate lever 158 to rotate cylinder lenses 38B and note the ultimate position of lever 158 relative to scale 162. If both lens bars 14' and 18' include cylinder or crossed-cylinder lenses 38B and levers 158, manipulation of the levers 158 produces independent rotation of pairs of such lenses 38 aligned with collar aperture 94 and line of sight 98, in accordance with the teachings of some of my patents and applications referenced above. I situations where non-spherical lenses 38 are included in both lens bars 14' and 18' (or in lens bars 14 and 18), lens 30 may be used to determine the sphere lens providing the best vision. Using a sphere lens as lens 30, cylinder lenses 38B of greatest power in the 90/180° meridians in one of lens bars 14' and 18' (or lens bars 14 and 18), and cylinder lenses 38B of greatest power in the 45/135° meridians in the other, for example, permits correction of virtually all human optical errors.

The foregoing is provided for the purpose of illustration, explanation, and description of embodiments of the present invention. Modifications and adaptations to these embodiments will be apparent to those of ordinary skill in the art and may be made without departing from the scope and spirit of the invention.

I claim:

1. Optical apparatus comprising:
   a. a first bar defining (1) a longitudinal axis, (2) a track parallel to the longitudinal axis, and (3) a plurality of apertures;

b. a lens (1) positioned within each aperture and along the longitudinal axis of the first bar and (2) defining an axis of rotation perpendicular to the longitudinal axis of the first bar; and c. a collar, defining (1) a recess adapted to be engaged by the track of the first bar for movement along the first bar and (2) an aperture for alignment with any selected lens of the first bar.

2. Optical apparatus according to claim 1 further comprising means for determining the angular rotation of any selected lens about its axis of rotation.

3. Optical apparatus according to claim in which the aperture of the collar is adapted to receive a removable lens.

4. Optical apparatus according to claim 3 in which the angular rotation determining means comprises:
   a. a tube connected to the optical apparatus;
   b. a viscous fluid and a mercury bead within the tube; and
   c. a scale positioned adjacent the tube.

5. Optical apparatus according to claim 4 further comprising:
   a. a second bar, adapted to be positioned adjacent and moveable relative to the first bar, defining (1) a longitudinal axis, (2) a track parallel to the longitudinal axis and adapted to be engaged by the collar, and (3) a plurality of apertures; and
   b. a lens positioned within each aperture and along the longitudinal axis of the second bar, (2) defining an axis of rotation perpendicular to the longitudinal axis of the second bar, and (3) having a cylindrical component.

6. Optical apparatus according to claim 3 in which the angular rotation determining means comprises:
   a. a toothed annulus encircling each lens of the first bar;
   b. a rack (1) positioned at least partially within the first bar and (2) comprising a plurality of teeth for engaging the toothed annulus of each lens of the first bar;
   c. means for moving the rack; and
   d. a scale associated with the rack moving means.

7. Optical apparatus according to claim 1 further comprising a second bar (1) adapted to be engaged by the collar and (2) positioned adjacent the first bar.

8. Optical apparatus according to claim 7 in which the track defines a plurality of notches and the collar comprises a leaf spring adapted to engage at least one selected notch.

9. Optical apparatus according to claim 8 in which the collar further defines an annular recess for permitting attachment of the collar to other apparatus.

10. Optical apparatus comprising:
    a. a first bar defining (1) a longitudinal axis, (2) a track parallel to the longitudinal axis and defining a plurality of notches, and (3) a plurality of apertures;
    b. a lens (1) encircled by an annulus comprising a plurality of teeth, (2) positioned within each aperture and along the longitudinal axis of the first bar, and (3) defining an axis of rotation perpendicular to the longitudinal axis of the first bar;
    c. a moveable rack, at least partially positioned within the frame, for simultaneously engaging each annulus and thereby rotating each lens of the first ba about its axis of rotation;
    d. means, attached to the rack, for moving the rack and indicating the angular rotation of each lens of the first bar as a function of movement of the rack;
    e. a second bar positioned adjacent and moveable relative to the first bar and defining (1) a longitudinal axis parallel to the longitudinal axis of the first bar, (2) a track parallel to the longitudinal axes and defining a plurality of notches, and (3) a plurality of apertures, each containing a lens; and
    e. a collar, comprising a leaf spring for engaging at least one selected notch of each of the tracks of the first and second lens bars, defining (1) a plurality of recesses adapted to be engaged by the tracks of the first and second bars for movement along the first and second bars and (2) an aperture for receiving a removable lens for positioning along any selected one of the axes of rotation.

11. A method for determining the refractive error of a patient, comprising the steps of:
    a. viewing through an aperture at least one lens of a plurality of lenses contained on a first lens bar;
    b. moving, relative to the first lens bar and the aperture, a second lens bar positioned adjacent the first lens bar and containing a plurality of lenses;
    c. viewing through the aperture at least one lens of each of the first and second lens bars; and
    d. rotating at least one of the viewed lenses while continuing to view through the aperture.

12. A method according to claim 11 further comprising the step of determining the angle of rotation of the viewed lens.

* * * * *

UNITED STATES PATENT AND TRADEMARK OFFICE
CERTIFICATE OF CORRECTION

PATENT NO. : 5,285,224
DATED : February 8, 1994
INVENTOR(S) : Clinton N. Sims

It is certified that error appears in the above-indentified patent and that said Letters Patent is hereby corrected as shown below:

Column 1, line 53, delete the word "ar" and insert --are-- therefor

Column 2, line 61, delete the word "lens" and insert --lenses-- therefor

Column 3, line 13, delete "15" and insert --18-- therefor

Column 4, line 48, delete the word "I" and insert --In-- therefor

Column 5, line 13, after the word "claim" insert --2--

Column 5, line 30, after the word "lens" insert --(1)--

Column 6, line 17, delete the word "ba" and insert --bar-- therefor

Signed and Sealed this

Fifth Day of September, 1995

Attest:

BRUCE LEHMAN

*Attesting Officer*  *Commissioner of Patents and Trademarks*